United States Patent [19]

Hogan

[11] Patent Number: 5,758,892

[45] Date of Patent: Jun. 2, 1998

[54] RESTRAINT CHAIR

[76] Inventor: Thomas Hogan, 31 N. 16th St., Denison, Iowa 51442

[21] Appl. No.: 630,634

[22] Filed: Apr. 10, 1996

[51] Int. Cl.[6] ............................................ B62M 1/14
[52] U.S. Cl. .............................. 280/250.1; 297/466
[58] Field of Search ........................ 280/250.1, 304.1, 280/47.18, 47.24, 47.25, 47.33; 297/466, 464, DIG. 4; 128/876, 869

[56] References Cited

U.S. PATENT DOCUMENTS

| | | | |
|---|---|---|---|
| 4,509,797 | 4/1985 | Mallaly | 297/466 |
| 4,593,929 | 6/1986 | Williams | 280/650 |
| 4,645,262 | 2/1987 | Furabotten | 297/129 |
| 4,728,553 | 3/1988 | Daniels | 297/466 X |
| 4,887,837 | 12/1989 | Bonewilz | 280/654 |
| 4,930,842 | 6/1990 | Wilkinson et al. | 297/466 |
| 5,451,092 | 9/1995 | Gray | 297/466 X |

*Primary Examiner*—Christopher P. Ellis

[57] ABSTRACT

A chair device in which a hyperactive patient or prisoner can be held and moved about while maintaining control of the person and moved without undue force. The chair includes restraining straps for the seat, arms, legs and shoulders, and is provided with wheels by which it can be moved and handled for use by the mover.

9 Claims, 1 Drawing Sheet

RESTRAINT CHAIR

BACKGROUND AND SUMMARY OF THE INVENTION

This invention pertains to devices intended to restrain a resistant, violent or hyperactive person, and still to allow that person to be moved from place to place. It is especially useful in moving people who are incarcerated in prisons or jails or who may be confined to hospitals for treatment of mental disorders.

Often it is necessary to move a recalcitrant person either in hospitals or in prisons or jails from one location to another. These times might include times for movement from a room or cell to a consultation room for an interview with a doctor or from a cell to a courtroom for pre-trial hearings or for trial. Most people are able to walk more or less willingly for the purpose. However, there is the occasional person who will object and either become violent or simply refuse. For those people, more urgent persuasion than simple words may be necessary.

This present invention provides a device by which a person who may refuse to walk may be placed in a chair, restrained there and then may be readily wheeled to the locale where his or her presence is required.

DESCRIPTION

Briefly, this invention pertains to a device for moving recalcitrant persons from one location to another—usually against their will. The need is for a device convenient to use without requiring undue force or violence.

More specifically and with reference to the drawings, the proposed device includes a chair having a back 10 and a seat 11. These parts are mounted on a frame which may use tubular members as its structural parts.

Figure 3:
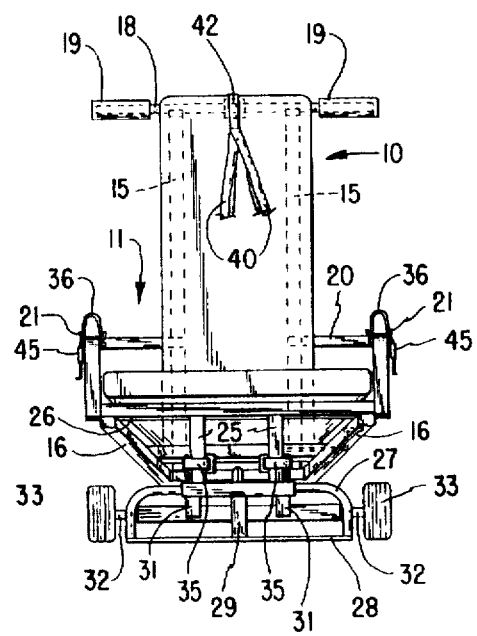
FIG. 3 is a front elevational view of the chair.

The frame includes substantially parallel back support members 15 and seat supports 16 which may diverge from the parallel (FIG. 3) but may be formed of the same piece merely bent from the back supports 15. From the side elevation, the angle between back support 15 and the seat support 16 is of the order of 100° to 120°. The seat supports 16 also slope downward to the rear at an angle of between 10° to 20° to the floor. These slopes are important to the use of the device.

The sloping seat supports allow the prisoner to be seated at a relatively low level above the floor and still comfortably hang his or her legs over the front edge of the seat. The angle between the seat supports 16 and the back supports 15 is important principally for the reasonable comfort of the occupant of the seat. At the same time, the tilt of the body does allow a more convenient location for the fulcrum around which the chair is tilted as will appear.

Figure 1:
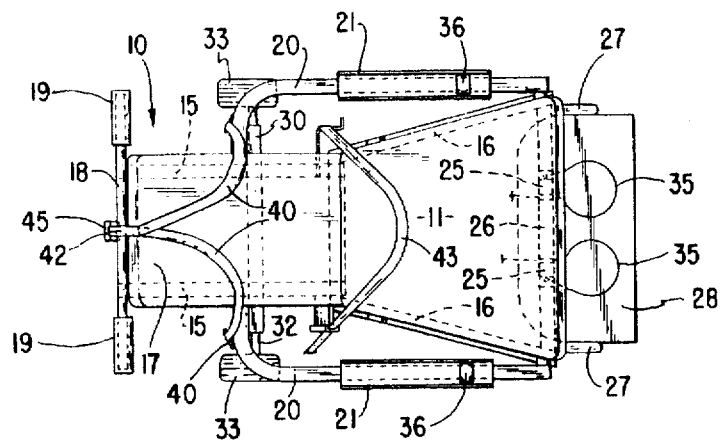
FIG. 1 is a top plan view of the chair.
Figure 2:
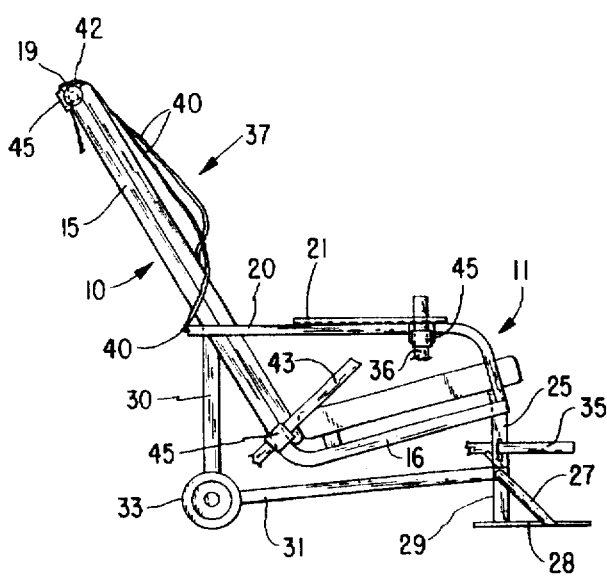
FIG. 2 is a side elevational view of the chair.

As shown in FIG. 1, the spacing between the back supports 15 and therefore the width of the back 13 is relatively narrow. The narrowness does not seriously affect the comfortability of the chair, but it does make possible the use of a crossbar or handle bar 18 for use in handling the chair. Handle grips 19 are provided at the ends of the crossbar 18 for use by the person handling the chair.

As part of the frame, arms 20 are fastened to the back supports 15. As best shown in FIG. 1, the member which forms the arms 20 may be bent to hold the back and be fastened to the supports there. It then runs forward to form the arms 20. Arm holders 21 are provided to form the top surfaces of the arms 20.

The front legs 25 of the chair are fixed to a transverse member 26 extending between the seat supports 16 and holding the forward end of the arms 20. At the end of the front legs, an arched ankle rest member 27 is fastened and extends downwardly where it is attached to a foot plate 28. This plate is adapted to support the occupant's feet so they cannot be used to interfere with movement of the chair. For additional strength, a center support 29 may be used.

At the rear of the chair a rolling mechanism is provided. This mechanism includes a pair of rear legs 30 and a pair of reach members 31 meeting to form vertices to which a transverse axle 32 is fixed. The reach members 31 extend from the rear legs 30 to the front legs 25. Wheels 33 are journalled on the axle 32 so that when the chair is tilted back onto the wheels, the entire chair can readily be moved carrying the occupant.

In most cases added restraint is needed. For that purpose various belts and straps may be provided. Such straps are customarily used in vehicles such as cars and airplanes and are made of a nylon webbing or the like. In this chair, ankle straps 35 may be provided fastened to the front legs 25 of the chair. These straps are for restraining the legs of the occupant. They are fastened to the chair leg at one end and may be wrapped around the ankles of the occupant and returned to the leg 25 where a fastening means such as a buckle 45 or a hook and loop fabric fastener is provided to hold the restraint in place.

Similarly, wrist straps 36 may be used on the arm holders 21 to restrain the arms of the occupant. The shoulder restraint 37 adapted to hold the shoulders of the occupant may be a Y-shaped belt having the two arms 40 of the Y fastened to the rear end 41 of the arms and extending upward to the leg 42 of the Y shape. The leg 42 can then be fastened to the center of the bar 18 by a single buckle 45 or hook and loop fabric fastener.

If desired, a lap belt 43 similar to lap belts in automobiles or planes may also be used.

In use, the chair may be moved behind the proposed occupant who is in custody. That person can then be seated on the seat either voluntarily or with suitable force. If necessary, the person may be lifted onto the seat. It is in such occasions that the lower level of the seat may be helpful. After the person is seated, the restraints are fastened so that the person is relatively immobile—at least to the point where he or she will not interfere with movement of the chair.

The operator can then tilt the chair rearward by use of the handle grips 19 and roll the chair and its occupant to the desired place. It will be noted that the rearward tilt of the back 17 moves the general center of gravity to the rear so that tilting the chair is less burdensome then if the entire body of the occupant were straight up in front of the axle 32.

Thus, a useful device for moving recalcitrant people who must be moved is provided. The device is especially useful with prisoners or mentally ill patients who may become violent or simply resistant to being moved.

I claim as my invention:

1. A transporting device for use in carrying a recalcitrant person from one location to another over a relatively hard surface, said device comprising a chair having a seat and a back held together at an angle of between 100° and 120°, arms extending alongside and above the level of said seat, front legs extending from the seat to a position in which to contact said surface, fixed brackets extending downwardly from a position on said back between the top of said back and said angle between said seat and said back, said brackets extending towards said surface and, wheels journalled on said brackets beneath said back whereby said chair may be rolled over said surface by tilting the chair backward and will be held in position by tilting the chair forward so that said front legs contact said surface.

2. The device of claim 1 in which said front legs are connected by a foot plate extending forward from said front legs to interfere with contact between the feet of the person with said surface.

3. The device of claim 1 in which a transverse bar is fixed to the upper part of said back to provide handles to control said rolling of the chair.

4. The device of claim 1 in which restraints are fixed to said chair to control movement of said recalcitrant person when occupying said chair.

5. The device of claim 4 in which said restraints are fastened to said chair on said back, on said arms and on said front legs, said restraints on said front legs being positioned to control the ankles of said recalcitrant person.

6. The device of claim 4 in which said restraints are straps fixed to said device in position to control the shoulders, arms and legs of said recalcitrant person.

7. The device of claim 1 in which an axle extends between said brackets, said wheels being journalled on said axle.

8. The device of claim 1 in which said seat slopes downwardly from the front of said seat relative to said surface at an angle of between 10° and 20°.

9. The device of claim 1 in which a lap belt is fixed to said chair to form a restraint for the torso of said recalcitrant person.

* * * * *